United States Patent [19]

Posner

[11] 4,049,534
[45] Sept. 20, 1977

[54] ELECTROPHORECTIC APPARATUS FOR ELUTION FROM PREPARATIVE GELS

[75] Inventor: Israel Posner, Caracas, Venezuela

[73] Assignee: E-C Apparatus Corporation, St. Petersburg, Fla.

[21] Appl. No.: 676,178

[22] Filed: Apr. 12, 1976

[51] Int. Cl.² .......................................... G01N 27/28
[52] U.S. Cl. ............................ 204/299 R; 204/180 G
[58] Field of Search ............... 204/180 G, 180 P, 299, 204/301

[56] References Cited
U.S. PATENT DOCUMENTS

| | | | |
|---|---|---|---|
| 3,470,080 | 9/1969 | Raymond et al. | 204/180 G |
| 3,523,879 | 8/1970 | Cortes | 204/301 X |
| 3,718,559 | 2/1973 | Wallace | 204/180 G |
| 3,719,580 | 3/1973 | Roberts et al. | 204/299 |
| 3,751,356 | 8/1973 | Takeya et al. | 204/301 X |
| 3,822,197 | 7/1974 | Nees et al. | 204/180 G X |
| 3,888,758 | 6/1975 | Saeed | 204/299 |
| 3,989,612 | 11/1976 | Kragt et al. | 204/180 G |

*Primary Examiner* — Arthur C. Prescott
*Attorney, Agent, or Firm* — Sughrue, Rothwell, Mion, Zinn and Macpeak

[57] ABSTRACT

A multiple cell electrophoresis elution device is disclosed. Gels are fractionated to locate, by scanning, the component of interest and the gel is sliced to isolate this band. In one embodiment, it is then placed in one compartment of the elution device and recast in place using a dilute gel. This recasting mechanically holds the gel and acts as a separating barrier from one buffer compartment to another. The gel casting procedure prevents both dilution of the eluted fractions by mixing due to mechanical or convective influences as well as insuring that the current must pass through the gel and not around it in the more conductive free buffer. In another embodiment, the cut gel is covered with an element to occupy the remaining volume of the gel compartment and compress the gel.

The device employs a series of compartments joined to a single set of electrodes such that a number of distinct separate fractions may be eluted simultaneously. Also, various operating parameters can be varied from the electrophorectic separation to yield more pure elutes. The membranes used to separate the cells are affixed using a wax paper and grease seal which effectively prevents leakage.

9 Claims, 6 Drawing Figures

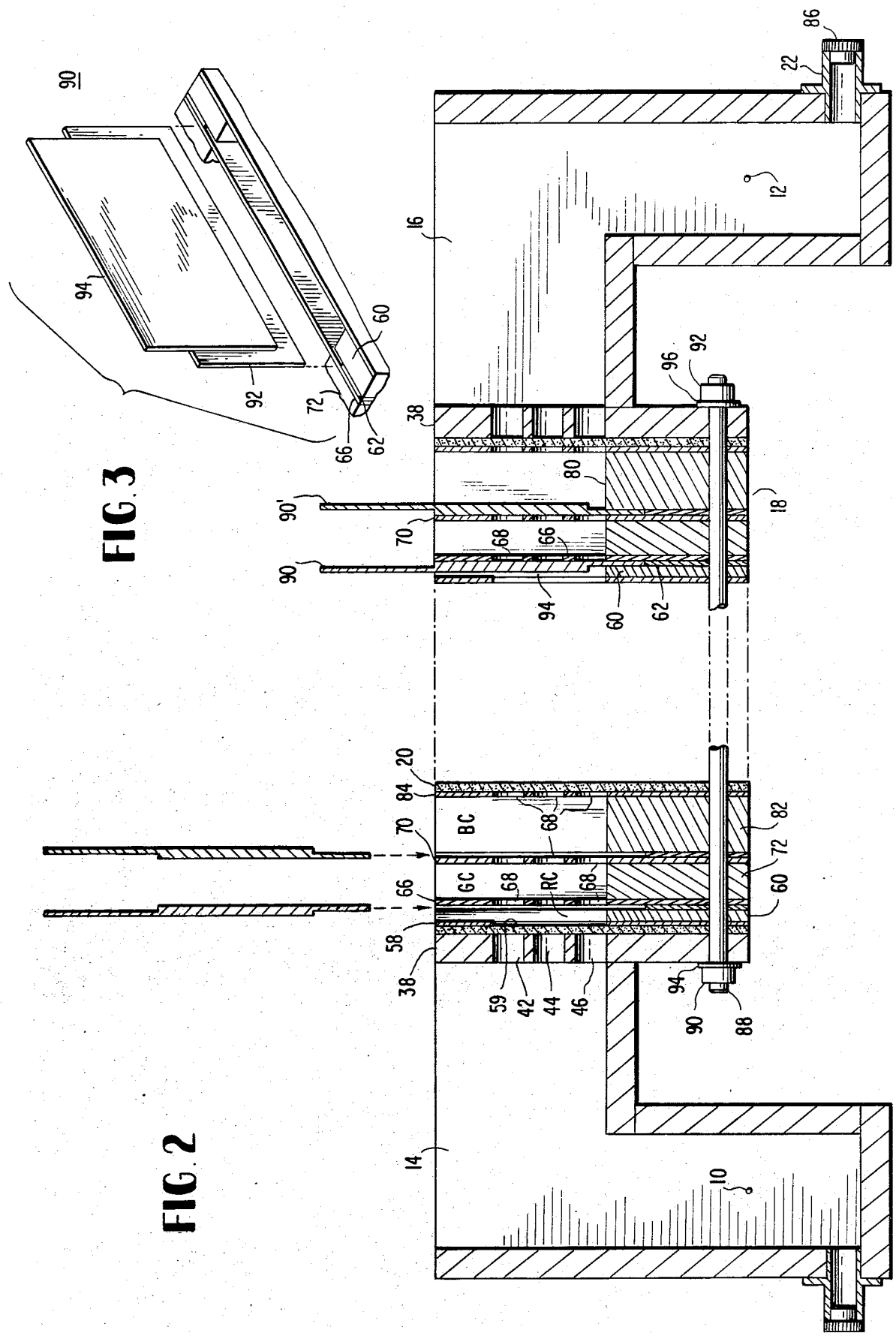

ELECTROPHORECTIC APPARATUS FOR ELUTION FROM PREPARATIVE GELS

BACKGROUND OF THE INVENTION

1. Field of the Invention

This invention relates to the field electrophoresis using multiple recovery cells for cast gels.

2. Prior Art

The prior art is replete with descriptions of apparatus and empirical results of the practice of electrophoresis. Electrophoresis can generally be defined as the movement in an electric field of charged molecules in any substance, typified by inorganic ions, proteins, enzymes, and blood serum. The basic operating principle is that any charged particle suspended between the poles of an electrical field tends to travel toward the pole that bears the charge opposite to its own. The rate of travel is conditioned by a variety of factors including the characteristics of the individual particle, the properties of the electrical field and operating parameters such as temperature and the nature of the suspending medium or buffer.

These fundamental principles of electrophoresis have been known since the 1920's [See: "Advances In Protein Chemistry" edited by M. L. Arsen and John T, Edsall, Vol. IV, pp. 272–277 (1948)].

While the subject of much academic interest, the practical application of these electrophorectic principles presented many practical difficulties such as leakage, heat generation and the inordinate length of time needed for yielding meaningful results. The mobilities of molecules under study can be established only with experimental data under reproducible circumstances and, accordingly, the control of environment and operating conditions have been a major hurdle to overcome in the prior art. An early solution is typified in U.S. Pat. No. 2,758,966 wherein in a dispersion a horizontal electrical field is created which causes a horizontal migration of colloid particles in the dispersion. This horizontal migration proceeds until vertical barriers of semipermeable membranes are reached where the migration is stopped and the particles accumulate. The differences in density in the dispersion near the membrane as a result of the accumulation of the charged particles creates a convection current transporting distinct components at different rates thereby accomplishing the desired separation. This type of device typifies so-called free-solution electrophoresis and the prior art contains a variety of such devices such as in U.S. Pat. Nos. 3,047,489 and 3,129,158.

Another technique of importance in the prior art is that of providing a bed or support onto which the electrophorectic process can take place both for analysis and separation. An early technique was to use filter paper, however, there have been problems of diffusion and absorption of the molecules to the paper. This generally results in a loss of definition in separation as well as losses of 10–15 percent in accumulated content (See: U.S. Pat. No. 2,555,487). U.S. Pat. No. Re. 24,752 sought to minimize these losses by using a fluid film as the medium. A gelling agent is employed in the buffer such that although the buffer is a liquid, at small angles of tilt, if applied to a glass plate, there would be no movement of fluid. In practice, this film is placed on a glass plate and the particular composition to be analyzed is added by placing a small piece of filter paper which has been soaked in the material onto one end of the plate and the electric field is applied. While techniques such as this are suitable for analytical electrophoresis they are totally not adaptable for the collection of the isolated component fraction.

The prior art has also attempted to accomplish separation by the use of supporting gels as typified by U.S. Pat. No. 3,450,624. A large amount of gel is used as the support medium, cast vertically, to which the sample is added and electrophoresis takes place horizontally across the gel with eludes collected at the base. Devices such as in this patent rely on long running times to accomplish separation with the attendant problems of heating. It is evident that maintaining uniform temperatures during long runs becomes a governing criteria which has heretofore made gel support mediums generally unsatisfactory for elution or collection electrophoresis. Attempts to minimize these difficulties have resulted in the use of cut pieces of gel on a screen with elution taking place with a bag composed of dialysis tubing [Haschke and Campbell, J. Bac. 105,249 (1971)] for sample elution. Similarly, U.S. Pat. No. 3,255,100 describes an improved apparatus for the collection of the isolated component fraction in its pure state without the presence of other substances such as the supporting medium.

According to the teachings of the Raymond patent, after one electrophoresis run in which the components of a complex substance are separated on the supporting gel, this gel is then placed in an electrophoresis cell with the gel oriented vis-a-vis the electrodes such that migration occurs under the influence of the electric field with the fractions maintained separately during movement by a separating block. When the dialysis membrane is reached a series of vertical channels allow the accumulation by gravity in a convection current of the separated components into suitable collection receptacles.

Devices such as Raymond allow for the collection of individual fractions from a single gel, however, the elution of a number of separate fractions has heretofore not been feasible.

SUMMARY OF THE INVENTION

This invention overcomes the difficulties inherent in the prior art by utilizing a gel containing the desired fraction that is in one preferred embodiment, recast in the holder of the electrophoresis device. This casting in place develops a specific hydraulic and electrical barrier between buffer compartments. The hydraulic barrier prevents dilution of the eluted fractions as a result of mixing due to mechanical or convective influences. The electrical barrier insures that the current must pass through the gel and not around the gel in the more conductive free buffer. In a second preferred embodiment, the cut gel is covered by an element which occupies the remaining volume of the gel compartment.

The elution device uses a number of cells joined in series to one set of electrodes to thereby elute a number of separate fractions. Between the cells, the dialysis membrane pore size can be varied for the retention of eluted molecules on the basis of molecular weight. Additionally, the problem of leakage around the membrane, a common problem in the prior art, is solved by the use of a grease and wax paper coating sealed against the sides of the cell by mechanical pressure. Since in the design, the cells are configured to take advantage of electrodecantation, the macromolecules are recovered in relatively small volumes.

Accordingly, it is an object of this invention to provide a method of elution electrophoresis that employs cut gels which are recast in place in the cell of the apparatus.

It is another object of this invention to provide a method of electrophoresis whereby a number of separate fractions can be eluted simultaneously.

A further object of this invention is to provide a method of elution of identified fractions in a gel utilizing a recasting technique that develops hydraulic and electrical barriers between buffer compartments.

These and other objects and features of the invention will be understood from the following description of the preferred embodiments taken in conjunction with the drawings.

BRIEF DESCRIPTION OF THE DRAWINGS

FIG. 2 is a plan view of the apparatus of the present invention showing two cells and the disposition of spacers.

FIG. 3 is a perspective view showing the location of a spacer in a particular cell.

DETAILED DESCRIPTION OF THE PREFERRED EMBODIMENTS

Figure 1:
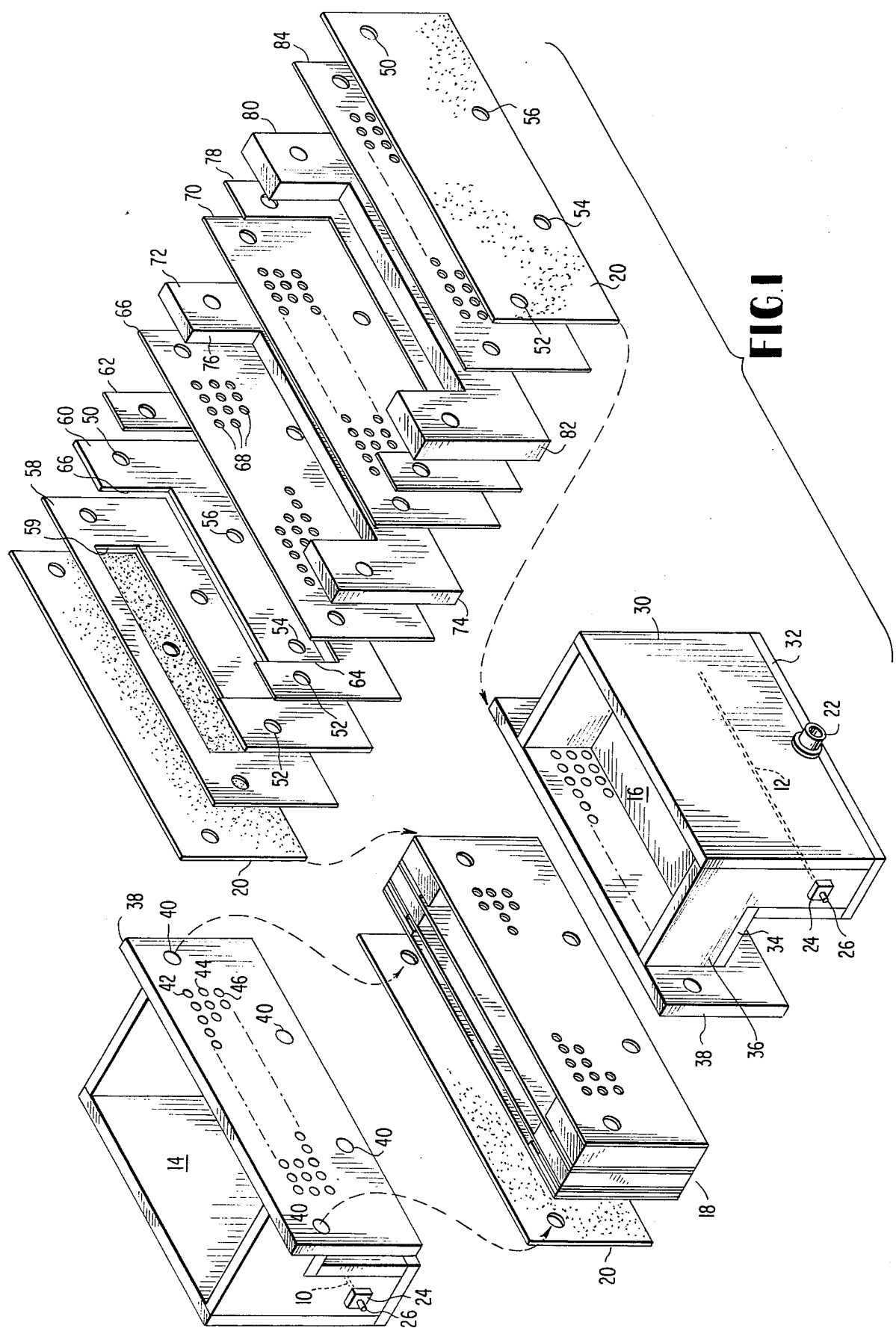
FIG. 1 is a perspective view of the apparatus of the present invention showing an exploded section which comprises one cell.

Referring now to FIG. 1, a perspective view of the apparatus of the present invention is shown. The entire instrument for carrying out electrophoresis is constructed of Plexiglas except for platinum electrodes, their terminals and a series of bronze screws which are used to hold the components together. In its most basic form, the apparatus of FIG. 1 is composed of an anode 10 and a cathode 12 with electrode buffer compartments 14 and 16. A series of recovery cells 18 are separated from each other by dialysis membranes 20 and outlet compartments 22 in both the buffer compartments 14 and 16 are used for the purpose of emptying the buffer solution. The anode 10 and cathode 12 are comprised of platinum wires which extend longitudinally across each buffer compartment 14 and 16 and have terminal ends 24 which plug receptacles 26 for purposes of coupling the source of electrical energy to the unit.

The components which comprise the electrode buffer compartments are fashioned from Plexiglas, however, other suitable materials may be used. These compartments are mirror images of each other and for purposes of discussion the construction of element 16 is exemplary. The buffer compartment 16 is composed of a generally inverted L-shaped section comprising a back wall 30, a base plate 32 and an upper section of the inverted L having a base plate 34 coupled to the underside of the inverted L section which is generally denoted at 36. Baffles 38 are glued to recovery compartments 14 and 16 and comprise a sheet of Plexiglas drilled as follows. These baffles extend and have overlaps on each of the buffer compartments as shown schematically in FIG. 1. Four holes 40 are drilled through these baffles for the purpose of attaching by screws, the recovery chambers which are placed in between baffles 38. Each baffle has a series of holes drilled through it in a plurality of rows, typically as shown in FIG. 1 as being three rows 42, 44 and 46 which have holes which may be approximately 5 mm. in diameter drilled through them. Baffles 38 are glued to each electrode buffer compartment 14, 16.

Between these baffles a series of recovery cells may be placed in an operative arrangement. As shown in FIG. 1, two such cells may be utilized, however, in practice the number may vary continuously from 2 up through approximately 10 cells. The exact number of cells used depends on the number of materials to be recovered by electrophoresis and the strength of the applied electric field. As shown in the exploded section of FIG. 1, the elements comprising an individual recovery cell are shown in an exploded fashion. Each cell is separated from the other by a dialysis membrane 20, to be discussed in detail later, and comprises a series of separator and baffle elements. Each dialysis membrane has a series of holes 50, 52, 54 and 56 which are drilled through it and correspond to the holes 40 and the baffles 38 which are used to couple the entire apparatus.

Referring now in detail to the exploded section shown in FIG. 1 an end plate 58 is used to define in one end of the recovery cell 18. This end plate is generally rectangular in form containing holes located in the same position as those in the dialysis membrane for the linking of the elements. Also, the generally rectangular open space 60 is used to permit the passage of fluid through the cell. The end plate is fashioned of Plexiglas as are the other elements forming the constituent sections of the recovery cell. Immediately adjacent to end plate 58 is a first U-shaped member 62. The element 60 defines the section in the recovery cell which is the recovery compartment and is small, in the order of 2 mm. thick. A series of holes 50, 52, 54 and 56 are used in operative alignment with the other elements to provide a screw attachment to the entire cell. Disposed immediately adjacent to the U-shaped member 60 is a spacer 62 which corresponds in longitudinal dimension and height to the other elements of the cell. However, the spacer has an inside depth along wall 64 greater than the inside depth along wall 66 of element 60. The function of the increased depth is for the placement of a separator element between compartments of the recovery chamber which will be described in detail later on. Immediately adjacent to spacer element 62 is a baffle 66 which comprises a series of holes in three rows 68. Each row 68 contains 16 holes which are drilled in the center part of the baffle. It is apparent that the size and number of holes may be varied to insure free mixing. The thickness of the baffle 66 is identical to that of end plate 58 and an identical baffle 70 is also shown in the exploded view. Disposed between baffles 66 and 70 is a second U-shaped member 72 which is used to define the gel compartment of the recovery cell 18. The gel compartment has a base 74 and the height of the compartment along wall 76 is the same as the recovery compartment 60. Disposed immediately adjacent to baffle 70 is a second spacer element 78 which is identical in construction to first spacer 62. Defining the third compartment of the recovery cell is a generally U-shaped member 80 which has a base 82 and generally defines the area in the recovery cell where the buffer to be used is placed. Between element 80 and dialysis membrane 20 is a third baffle 84 identical in construction to elements 66 and 70 and need not be discussed in detail.

The recovery cell comprising elements 58, 60, 62, 66, 70, 72, 78, 80 and 84 are held together by a series of four bronze screws which extend through holes 50, 52, 54 and 56 and are used to compress the elements into a completed cell as shown as 18 in FIG. 1. A series of such cells of identical construction may be placed in a FIG. 1 apparatus separated by dialysis membranes 20.

Referring now to FIG. 2, a side view of a completed apparatus showing two such recovery cells is schematically shown. In FIG. 2, the buffer compartments 14 and 16 have outlets 22 with end plugs 86 attached therewith showing the retention of buffer fluid in these compartments. The anode electrode 10 and cathode electrode 12 are shown extending through the compartment. As better shown in this side view, one bronze screw 88 is shown extending through the entire assembly and holding the elements in compression by means of nuts 90, 92 and washers 94 and 96. Additionally, the elements comprising an individual recovery cell 18 are glued together.

The view in FIG. 2 clearly shows that the three rows of holes 42, 44 and 46 in the baffles 38 are in operative alignment with the rows of holes 68 in the baffles 66, 70 and 84. The opening 60 in end plate 58 also provides an equivalent area extending the operative width of the recovery cell to allow the flow of buffer solution therethrough. Not shown in these figures is a conventional pumping means to maintain fluid level and circulate buffer solution.

FIG. 3 shows schematically the construction of an individual spacer which is used to separate the three compartments of the recovery cell and its position vis-a-vis the operative elements of that section. In FIG. 3, the spacer is generally denoted at 90 and comprises a lower section which is a generally U-shaped member 92 and a thicker section 94 disposed on section 92 and extending up above the upper surface of element 92. As shown in FIG. 2, in the right hand side wherein a complete cell having two spacers is shown in place, one spacer 90 operatively fits into the space between 60 and 66 and rests on the inside top surface of generally U-shaped member 62. The section 94 of spacer 90 serves to block the flow of buffer through baffles 68 of element 66 and, similarly, a second spacer 90' fits into the adjacent space between elements 70 and 80. For purposes of discussion, the space in the compartment 18 defined by the element 60 will be called the recovery compartment and has been labelled RC in FIG. 2. Similarly, the space defined by element 72 will be denoted as the gel compartment and is labelled GC in FIG. 2. Also, the space defined by element 82 will be denoted in the discussion as the buffer compartment and is labelled BC in FIG. 2.

Membranes 20 separate the individual recovery cells from each other. These membranes are constructed typically as follows: parafilm (130 × 195 mm.) is folded in half with the sides which are away from the protective wrapping paper facing inward, thereby resulting in a double layered parafilm and paper with dimensions of 65 × 195 mm. The center section of the parafilm (but not of the wrapping paper) which is positioned away from the fold (40 × 105 mm.) is then cut-away. The faces of the parafilm which are on the inside, e.g., that is sides facing each other, are lightly greased with a high vacuum grease and a sheet of single thickness dialysis membrane (65 × 195 mm.) is inserted onto it. By the application of a slight pressure against the sides of the parafilm, the sides and bottom of the membrane become sandwiched between the two layers of the parafilm, while the center part will be protected between the two layers of wrapping paper. Holes are then punched in places corresponding to those indicated for all compartments for passage of screws 88 (one on each side corresponding to holes 50, 52 and two on the bottom corresponding to holes 54, 56). This "packaged membrane" may be stored in this form until it is needed for use in the electrophoresis device. Membranes need be replaced in the apparatus only in the case of accidental damage or other destruction which would reduce the efficiency of the unit and otherwise may be used for numerous runs.

The complete apparatus as shown in FIGS. 1 and 2 is assembled as follows. The screws 88 are inserted into the side and bottom holes 50, 52, 54 and 56 of the cell. The wrapping paper is removed from a package dialysis membrane and the outer sides of the parafilm are lightly greased although it should be noted that care should be exercised so as not to grease the exposed center part of the membrane. The membrane-parafilm sandwich is positioned so that the ends of the screws 88 which protrude from one side of the cell may be inserted through the holes of the sandwich and the latter is then carefully slid towards the cell. It is convenient to hold the cell in such a way that the screws are facing upward and the sandwich is gently pressed against the cell. When more than one cell is to be employed in the instrument, the additional cells are slid along the screws 88 on either side of the first cell and then a membrane-parafilm sandwich is slid into place on either side. In this manner, a stack of cells separated by membranes 20 can be compiled.

It should be noted that while assembling the apparatus, the cells should be oriented such that the recovery compartments RC (as defined by element 60) should be nearer the anode compartment 10 and the buffer compartment (denoted by the section 80) are therefore oriented nearer the cathode compartment 12. When the composite stack of recovery cells has been assembled, the elctrode buffer compartments are aligned so that the screws 88 may be inserted into the side and bottom holes of sections 38. Washers 94 and 96 are then slipped over the screws 88 and nuts 90, 92 are then firmly tightened so that all of the membranes are pressed hard against the compartment sections to prevent any potential leaks between adjacent components on either side of a membrane. After the apparatus is completely assembled, the parafilm-membranes 20, will stick out on the sides and tops of the cells and are trimmed off with a razor blade.

The operation of the device as shown in FIG. 1 is as follows. With the use of an E-C 470 apparatus (manufactured by E-C Apparatus Corporation of San Petersburg, Florida), proteins of interest are fractionated on 6 mm. gel slabs. The apparatus used is that of a single slot former with the model E-C 470. After this run, the gel is picked up with a spatula and transferred onto a gel holder. The slab is then trimmed by cutting one centimeter off of either side of the gel and a longitudinal 1 centimeter section of the gel is formed by cutting parallel lines through the gel center section. This section is removed and placed into a cuvet which is filled with enough buffer to cover the gel. This gel section is then scanned at 280 nm. for locating the protein band of interest and is then returned to its original position on the gel holder. During the scanning until the gel is ready for further slicing it may be covered with a saran wrap covered material to prevent evaporation from the buffer. The entire gel holder and its contents may be kept in a cold room or refrigerator.

After the distances through which the various protein bands have migrated have been determined from the UV scan as described above, the gel is sliced in appropriate positions in parallel with the bands such that each section contains the protein of interest for recovery. These gel sections, as sliced, are placed in the GC compartment of a recovery cell with the aid of a spatula. The spacers 90 are placed into slots defined by elements 62 and 78 on either side of the GC compartments and a newly prepared gel is transferred with the aid of a pipette into each GC compartment to a height of 2 cm. or enough to cover the sectioned gel. The newly prepared gel is identical in composition to the buffer and CYANOGUM 41 composition to the original gel as used in the E-C 470 apparatus electrophoresis run.

By this technique, the original gel is recast in place using the new gel such that it occupies the relevant area of the GC compartment of the apparatus. Following polymerization, a 0.01 concentration of the buffer used for preparing the gel is placed into the electrode compartments 14, 16, the BC and RC compartments to a height of 1 cm. from the top. The spacers 90 are then removed and the electrodes 10, 12 are connected to the power supply and current is passed through for the desired length of time.

At the end of a run, the spacer corresponding to the RC compartment (90) is reinserted into each cell and the proteins eluted into the RC compartments are recovered after stirring the buffer in the RC compartment with the aid of a disposable pipette. For purposes of protection of the gels and the samples, the buffer solutions and the entire apparatus are kept at 4° C prior to and during the recovery run. Currents used and the time of the run are a function of the particular buffer and the protein to be eluted.

With 0.04 M TRIS-HCl buffer, pH 8.6, serum albumin is quantitatively recovered in 2-3 hours with a current of 40 mAmp (200 volts ). Larger proteins, or even nucleic acids and ribosomes, may be recovered by an overnight run at an initial current of 25 mAmps.

EXAMPLE

Illustrative results of a sample experiment using the apparatus of the first preferred embodiment for separating and recovering serum proteins will now be presented. One and one-half ml of serum containing approximately 100 mg of total proteins was applied to a 6 mm. gel and proteins were fractionated by discontinuous electrophoresis. A 280 nm, scan of the gel was done on E-C model 470. The 280 nm. scan of the gel was completed in a conventional manner and the gel sliced. Aliquots of the original serum and of each of the recovered fractions were then subjected to qualitative discontinuous gel electrophoresis on 3 mm. gel slabs using an 8 slot former. Fractions number 4 and 5 numbers 6 and 7 were pulled. After dying with COOMASSIE BRILLIANT BLUE wR-250 and removing excess dye, the gels were sliced and each segment was scanned at .570 nm. Reasonably acceptable fractionation has been achieved. Obviously, there are more appropriate means of fractionating serum proteins. However, overall recovery (overnight run in the recovery apparatus under the same conditions as above) was better than 75% with 95% for albumin and 55–85% for globulins. The use of the technique has been successfully applied to the purification of some seed lectins and for the fractionation on the preparative scale of serum lipoproteins. The technique may find further application to the fractionation of nucleic nuclei acids and ribosomes.

It can be seen that the recasting procedure, that is of recasting the gel containing the protein of interest in the gel section of the apparatus develops various specific hydraulic and electrical barriers between buffer compartments. The hydraulic barrier actively prevents dilution of the eluted fractions by mixing due to mechanical or convective influences which are normally found in electrophoresis devices. The electrical barrier insures that the current must pass through the gel with the result of a very efficient eluting of the protein. This is in contrast to other devices wherein the current may be channeled around the gel into the more conductive free buffer. Also, it is apparent that employing a number of cells, joined to one set of eletrode compartments, a number of separate fractions may be eluted simultaneously.

Figure 5:
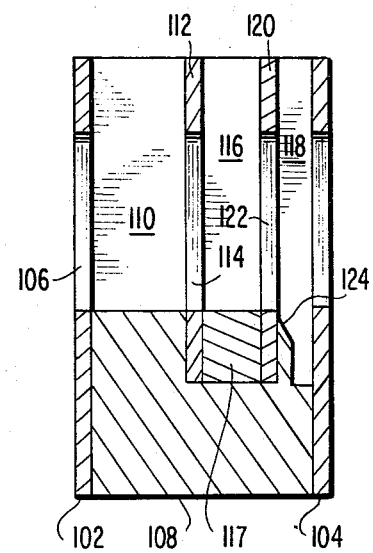
FIG. 5 is a side view of the cell shown in FIG. 4.
Figure 4:
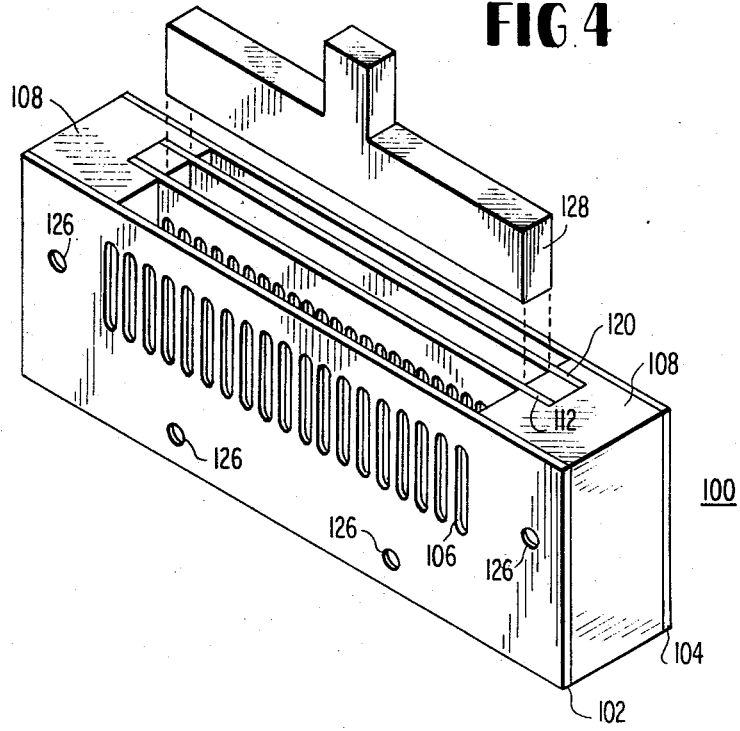
FIG. 4 is a perspective view of a cell in a second preferred embodiment of the invention.

A second preferred embodiment of a recovery cell is shown in FIG. 4. As in the prior embodiment, the device is constructed essentially of Plexiglas or another suitable material. As shown in FIGS. 4 and 5 the recovery cell 100 has two end baffle plates 102, 104 having a series of slots 106. The end plates are affixed by conventional means to base blocks 108 which is shaped to define the three compartments; buffer, gel and recovery of the cell. The buffer compartment 110 is defined by end plate 102 and a separator 112 having an array of slots 114 similar to those in plate 106. The gel compartment 116 is defined by spacers 112 and 120 and has a base 117 fashioned to have the same floor level as that of the buffer compartment. Slots 122 in spacer 120 are generally identical to those in outer spacers 104 and 106 but may, in some cases be higher to allow the elution of slightly wider gel sections. It is important that the bottom of the slots 114 and 122 be aligned with the level of the base members of the buffer and gel compartments otherwise proteins may become trapped below the current flow and will not migrate.

The recovery cell 118 is defined by spacer 120 and end plate 104 has a beveled section 124 to facilitate the elution into the recovery chamber 118. The bevel 124 is at a lower level than the floor of the gel compartment to eliminate any trapping of proteins between cells. As shown in FIG. 4, a series of holes 126 are drilled through the recovery cell to facilitate coupling individual cells into a composite unit by a series of bronze screws, not shown.

Also, shown in FIG. 4 is a "rider" or weight 128 configured to be of identical size as the gel compartment 116 and oriented to fit inside that compartment. This component is used to hold the gel slice in place and reduce the free volume in the gel compartment. The rider 128 squeezes the gel and insures that the current flow is through the gel and not around it in any stray conduction path.

Figure 6:
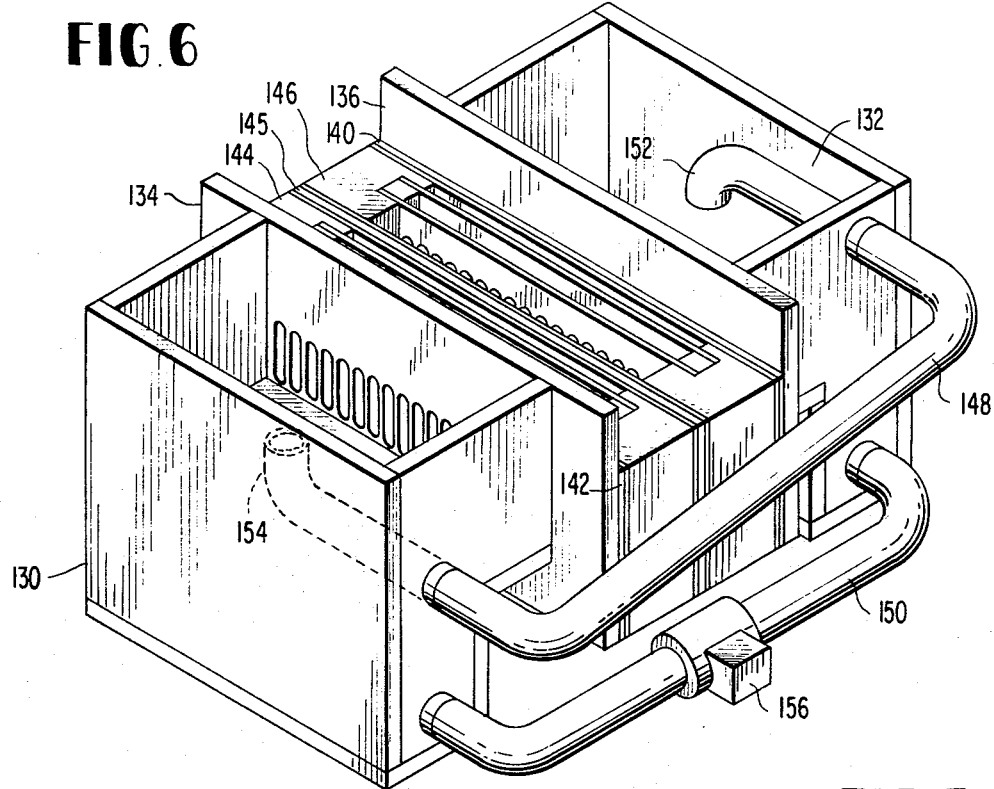
FIG. 6 is a perspective view of a completed device having two cells in accordance with the second preferred embodiment.

The general configuration of an assembled unit is shown in FIG. 6. Although two recovery cells are shown any number can be employed and eight of such cells appears to be an optimum number. In an arrangement similar to the first preferred embodiment, two buffer compartments 130 and 132 are employed, each with electrodes (not shown) disposed within and extending therethrough. Baffles 134, 136 and dialysis membranes 138, 140 are employed to separate the buffer compartments from the recovery cells. As in the fabrication of the first preferred embodiment, adjoining sections are lightly greased and an alternating series of cells 144, 146 and membrane sandwiches 145 are mounted along the bronze screws (not shown) until the recovery section is completed. The remaining buffer compartment is then slid into place and the entire unit is tightened by means of nuts on the screws. Once assembled, tubing 148 and 150 is inserted into buffer chambers 130 and 132 to operably link these chambers and member 152 and 154 for purposes of liquid level control well known in the art. A circulating pump is coupled to hose 150 at junction 158.

The operation of this device will now be discussed. At the conclusion of a first electrophoretic run to isolate the fractions of interest 0.75 cm are trimmed off both sides of the gel and the latter is transferred to a 10.5 × 15 × 1 cm Plexiglas receptacle. A longitudinal section, sliced perpendicularly to the protein bands at the center of the gel, is removed and scanned at 280 nm to locate the positions of the fractionated protein components. The scanned section is now returned to its original position and the entire gel is sliced into parallel sections each containing a protein band of interest. If the gel is scanned at a 1:1 ratio (a rate of 20 sec/cm in the Joyce Loebel UV scanner), the gel receptacle may be placed directly over the scan prior to slicing. Alternatively, protein bands may be located by staining a narrow longitudinal section of the gel while keeping the rest of the gel in Saran wrap till further sectioning. Sections may be as narrow as feasible (0.25 cm) but not wider than 1.5 cm, since material contained in a wider section will remain above the slots in the gel compartment of the recovery cell and will not be eluted.

Gel sections are transferred to the gel compartments 116 of respective cells of a recovery apparatus which is previously filled with 0.1 M Tris-Glycine buffer, pH 9.0, to the indicated levels. To each cell 30 ml of buffer need to be added. Next, riders 128 are introduced into each gel compartment to displace the buffer from above the gel sections. Current which crosses each cell is thus forced to pass through the gel and not through the buffer with its comparatively much lower resistance. This use of a weighted element such as 128 considerably hastens the rate of elution and notably improves recoveries of eluted materials and allows gel sections of different sizes to be used. Buffer is made to circulate between the electrode-buffer compartments 130, 132 and elution is carried out overnight at 100 v (20 mAmps). No change in current can be noted over this or much longer time intervals. It is advisable to use a proper cover over the entire recovery cell sections of the apparatus. When the electrophoretic elution is completed, the riders 128 are removed and the gel sections are very carefully removed with the aid of a spatula. Current may then be turned on again for a period of 2–3 hours at 30 mAmps to allow for the concentration by electrodecantation of any proteins which may diffuse from the recovery compartment 118 during the above manipulations. Buffer is now slowly withdrawn to the bottom of each buffer compartment and the solutions which remain in the bottom sections of the recovery compartments and which contain the eluted proteins (3.5 – 3.7 ml) are withdrawn with long tip dispensable-type pipettes. After the run the entire apparatus is washed with a diluted mild detergent solution and a stream of tap water followed by distilled water and allow to dry. It requires no further care between runs.

EXAMPLE

One ml of a 10.0% bovine serum albumin solution and 25% sucrose was applied to the slot of a 6 mm. thick polyacrylamide gel slab and the electrophoretic separation was carried out as described above. Except for a single peak at the origin, no UV absorbing material could be detected in the upper gel. Following electrophoretic elution as described, the recovered components were dialyzed against three changes of 0.154 M NaCl and protein concentrations were determined. The results shown in Table I below indicate that as much as 86.7% of the material applied to gel was recovered with 74.2% being recovered from sections $A_1 + A_2$ representing 85.7% of the total proteins recovered. After components B, C and D were concentrated, the various protein components were subjected to analytical electrophoresis using serum for comparisons. Gel preparations and electrophoretic conditions were the same as for the preparative run except that a 3 mm thick "upper-gel space-former" and a 3 mm 8-slot former were employed. The gels were stained with COOMASSIE BLUE. Component $A_1$ migrated entirely as a single band while component $A_2$ was slightly contaminated with component B. Component B contained about 15% component A and its relative migration was greater than that of the beta globulin. Components C and D were somewhat less homogeneous. It is assumed that component A represents the albumin monomer whereas components B, C and D molecular aggregates or contaminates of albumin.

TABLE I

| Component | Protein Concentration | Protein Discovered Total (Mg) | % Total |
|---|---|---|---|
| F | 0.06 | 0.2 | 0.2 |
| O | 0.0 | 0.0 | 0.0 |
| $A_1$ | 16.6 | 59.8 | 69.0 |
| $A_2$ | 4.1 | 14.4 | 16.6 |
| B | 2.0 | 7.1 | 8.1 |
| C | 1.0 | 3.8 | 4.4 |
| D | 0.4 | 1.4 | 1.6 |

The results obtained with bovine serum albumin demonstrate the effectiveness of the combined use of vertical gel slab electrophoresis and the recovery apparatus on a preparative scale. Up to 100 mg of proteins can be fractionated components with a fair amount of homogeneity can be achieved. For further purification, recovered components can be subjected to a second electrophoretic fractionation. Although this methodology is mostly indicated for later stages of purification, preliminary results obtained with systems more complex in composition than bovine serum albumin as well as with nucleic acids are quite encouraging.

The recovery apparatus, once assembled, is easy to manage and requires little attention. Special care should be taken only during the removal of the riders and the gel sections from the gel compartments and the withdrawal of buffer from the cell in order to prevent remixing of the concentrated macromolecules which are eluted into the recovery compartments. This apparatus may also be employed for concentrating macromolecules. Solutions should previously be dialyzed, however, against a demineralized fold buffer (e.g., Tris-Glycine). Concentrations of up to fifteen-fold can then be accomplished in relatively short times.

Although the present invention has been described in conjunction with the preferred embodiment, it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. An apparatus for elution electrophoresis of components separated by analytical electrophoresis comprising:
    a. a plurality of compartments containing a buffer solution;
    b. electrode means disposed within each compartment; and
    c. a plurality of recovery cells disposed between said compartments, said cells separated from each other and the compartments by dialysis membranes, each of said recovery cells having three sections, a first section holding buffer solution, a second section containing a gel having the component to be eluded, and a third section for recovering the elution.

2. The apparatus of claim 1 wherein baffles separate the three sections of said recovery cell from each other.

3. The apparatus of claim 2 including spacer means adapted to fit between said gel containing section and the other sections to isolate said gel section and wherein said spacer means are removable.

4. The apparatus of claim 3 wherein said gel is recast within said gel section to substantially occupy the entire volume of said gel section when said spacer means are positioned to isolate the gel section.

5. The apparatus of claim 4 wherein said recovery cells and said dialysis membranes are coupled to said buffer compartments by a series of screws.

6. The apparatus of claim 2 wherein the floor level of said recovery section of the recovery cell is at a lower level than the floor levels of the buffer section or the gel section.

7. The apparatus of claim 6 wherein the wall and floor between the gel section and the recovery section is beveled to prevent the isolation of proteins from the electric current generated between said electrode means.

8. The apparatus of claim 6 including means adapted to be placed in said gel section to compress said gel and prevent the passage of electric current around said gel.

9. The apparatus of claim 1 including means to maintain the liquid level of buffer in the buffer compartments and to circulate the buffer contained therein.

* * * * *